United States Patent
Roth-Chiarello

(10) Patent No.: US 8,329,640 B2
(45) Date of Patent: Dec. 11, 2012

(54) PEPTIDES WITH IMPROVED PROPERTIES HAVING THE BIOLOGICAL ACTIVITY OF VASOACTIVE INTESTINAL PEPTIDE (VIP) AND THEIR USE FOR THE TREATMENT OF LUNG DISEASES

(75) Inventor: Michael Roth-Chiarello, Sissach (CH)

(73) Assignee: RES International Sarl, Luxembourg (LU)

( * ) Notice: Subject to any disclaimer, the term of this patent is extended or adjusted under 35 U.S.C. 154(b) by 344 days.

(21) Appl. No.: 12/451,685

(22) PCT Filed: May 19, 2008

(86) PCT No.: PCT/EP2008/003989
§ 371 (c)(1),
(2), (4) Date: Nov. 20, 2009

(87) PCT Pub. No.: WO2008/141786
PCT Pub. Date: Nov. 27, 2008

(65) Prior Publication Data
US 2010/0256044 A1    Oct. 7, 2010

(30) Foreign Application Priority Data
May 21, 2007   (EP) .................................... 07010033

(51) Int. Cl.
*A61K 38/00*   (2006.01)
*A61K 38/16*   (2006.01)
*C07K 14/47*   (2006.01)
*C07K 5/00*    (2006.01)
*C07K 7/00*    (2006.01)
*C07K 16/00*   (2006.01)
*C07K 17/00*   (2006.01)

(52) U.S. Cl. ........................ 514/1.8; 514/21.3; 530/324

(58) Field of Classification Search ........................ None
See application file for complete search history.

(56) References Cited

FOREIGN PATENT DOCUMENTS
WO    WO 02/43746    6/2002

OTHER PUBLICATIONS

Thermo. N-Terminal Acetylation and C-Terminal Amidation of Peptides. Technical Information, 2004. TI-PEP01-1104. Germany. 2 pages.*
Shechter et al. Selective Oxidation of Methionine Residues in Proteins. Biochemistry, 1975, vol. 14, No. 20, pp. 4497-4503.*
French et al. What is a Conservative Substitution? J Mol Evol. 1983. vol. 19, pp. 171-175.*
Hruby. Designing Peptide Receptor Agonists. Nature Reviews, Drug Discovery, 2002. vol. 1, No. 2002, pp. 847-858.*
Ito, Osamu et al., "Vasoactive intestinal polypeptide precursors have highly potent bonchodilatory activity", Peptides (New York, NY, United States), 12 (1), 131-7; CODEN: PPTDD5; ISSN: 0196-9781, 1991, XP002500317.
Shirahase, H., et al., "Structure-activity relationships for relaxation of smooth muscle by VIP", Peptides (New York, NY, United States), 15(2), 383-5; CODEN: PPTDD5; ISSN:0196-9781, 1994, XP002500318.

* cited by examiner

*Primary Examiner* — Marcela M Cordero Garcia
(74) *Attorney, Agent, or Firm* — Perkins Coie LLP

(57) ABSTRACT

The present invention relates to novel peptides that are highly biologically and pharmacologically active as therapeutic agents for the treatment of numerous lung diseases or lung and/or bronchi related diseases, especially chronic obstructive pulmonary disease (COPD), cystic fibrosis (CF), and Bronchiolitis obliterans (BO). The synthetic peptides according to the invention are derivatives of vasoactive intestinal peptide (VIP) and show enhanced physical, pharmacological and biological/therapeutic properties compared to VIP.

9 Claims, 10 Drawing Sheets

SEQUENCE LISTING

<160> NUMBER OF SEQ ID NOS: 4

<210> SEQ ID NO 1
<211> LENGTH: 28
<212> TYPE: PRT

<213> ORGANISM: Homo sapiens

<400> SEQUENCE: 1

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 2
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: modified human sequence
<220> FEATURE:
<221> NAME/KEY: MOD_RES
<222> LOCATION: (1)..(1)
<223> OTHER INFORMATION: N-acetyl histidine
<220> FEATURE:
<221> NAME/KEY: MOD_RES
<222> LOCATION: (17)..(17)
<223> OTHER INFORMATION: methionine oxide

<400> SEQUENCE: 2

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: modified human sequence
<220> FEATURE:
<221> NAME/KEY: MOD_RES
<222> LOCATION: (1)..(1)
<223> OTHER INFORMATION: N-acetyl histidine

<400> SEQUENCE: 3

His Ser Asp Ala Val Phe Thr Asp Asn Tyr Thr Arg Leu Arg Lys Gln
1               5                   10                  15

Met Ala Val Lys Lys Tyr Leu Asn Ser Val Leu Asn
            20                  25

<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: modified human sequence
<220> FEATURE:
<221> NAME/KEY: MOD_RES
<222> LOCATION: (1)..(1)
<223> OTHER INFORMATION: N-acetyl histidine
<220> FEATURE:
<221> NAME/KEY: MOD_RES
<222> LOCATION: (17)..(17)
<223> OTHER INFORMATION: methionine oxide

<400> SEQUENCE: 4

```
His Ser Asp Ala Val Phe Thr Asp Asn Tyr Thr Arg Leu Arg Lys Gln
1               5                   10                  15

Met Ala Val Lys Lys Tyr Leu Asn Ser Val Leu Asn
                20                  25
```

PEPTIDES WITH IMPROVED PROPERTIES HAVING THE BIOLOGICAL ACTIVITY OF VASOACTIVE INTESTINAL PEPTIDE (VIP) AND THEIR USE FOR THE TREATMENT OF LUNG DISEASES

CROSS-REFERENCE TO RELATED APPLICATION

This application is a 371 National Stage entry of International Application No. PCT/EP2008/003989, filed May 19, 2008, published as WO 2008/141786 with an International Publication Date of Nov. 27, 2008, which claims priority to European Patent Application No. 07010033.4 filed May 21, 2007. These prior applications are hereby incorporated by reference herein in their entirety.

SEQUENCE LISTING

The instant application contains a Sequence Listing which has been submitted via EFS-Web and is hereby incorporated b reference in its entirety. Said ASCII copy, created on Apr. 30, 2010, is named 03099400.txt and is 2,367 bytes in size.

FIELD OF THE INVENTION

The present invention relates to novel peptides that are highly biologically and pharmacologically active as therapeutic agents for the treatment of numerous lung diseases or lung and/or bronchi related diseases, especially chronic obstructive pulmonary disease (COPD), cystic fibrosis (CF), and Bronchiolitis obliterans (BO) but also pulmonary and arterial hypertension (PH, AH).

The synthetic peptides according to the invention are synthetic derivatives/analogues of vasoactive intestinal peptide (VIP) and show enhanced physical and biological/therapeutic properties compared to wild-type VIP.

The present invention also relates to pharmaceutical compositions and formulations comprising said novel peptides for the use in lung diseases as specified, preferably by means of inhalation, including inhalation via nanoparticles.

BACKGROUND OF THE INVENTION

Chronic Obstructive Pulmonary Disease (COPD)

COPD is the overall term for a group of chronic conditions that are associated generally with the obstruction of lungs' airways. The disease may be accompanied by pulmonary hypertension (PH) but not necessarily. The term COPD refers in more detail to the following disorders: chronic bronchitis, bronchiectasis and emphysema.

Chronic bronchitis is an inflammatory disease that begins in the smaller airways within the lungs and gradually advances to larger airways. It increases mucus production in the airways and increases the occurrence of bacterial infections in the bronchial tree, which, in turn, impedes airflow. This chronic inflammation induces thickening of the walls of the bronchial tree leading to increasing congestion in the lungs that results in dyspnea. By definition, chronic bronchitis refers to a productive cough for at least three months of each of two successive years for which other causes have been ruled out.

Emphysema describes destruction of the lung architecture with enlargement of the airspaces and loss of alveolar surface area. Lung damage is caused by weakening and breaking the air sacs within the lungs. Several adjacent alveoli may rupture, forming one large space instead of many small ones. Larger spaces can combine into an even bigger cavity, called a bulla. As a result, natural elasticity of the lung tissue is lost, leading to overstretching and rupture. There is also less pull on the small bronchial tubes, which can cause them to collapse and obstruct airflow. Air that is not exhaled before the new inhale process gets trapped in the lungs, leading to shortage of breath. The sheer effort it takes to force air out of the lungs when exhaling can be exhausting.

Thus, the most common symptoms of COPD include shortness of breath, chronic coughing, chest tightness, greater effort to breathe, increased mucus production and frequent clearing of the throat. Patients are unable to perform their usual daily activities. Independent development of chronic bronchitis and emphysema is possible, but most people with COPD have a combination of the disorders. Both conditions decrease the lungs' ability to take in oxygen and remove carbon dioxide.

Long-term smoking is the most common cause of COPD, responsible for 80-90 to percent of all cases. Other risk factors are heredity, second-hand smoke, air pollution, and a history of frequent childhood respiratory infections. Cigarette smoking and other inhaled irritants plays a fundamental role in the pathogenesis of COPD, which affects as many as 8% of individuals in industrialized nations.

The inflammatory response in COPD involves a number of different cell types including mononuclear cells (macrophages), CD4+ and CD8+ T lymphocytes, neutrophils, which can be isolated from the lungs of patients with COPD. When activated, these cells induce mediators of inflammation and cytokines, such as interleukin (IL)-8, tumor necrosis factor-A (TNF-alpha), LTB4 which amplify the inflammatory response and may remodel lung architecture.

Moreover, there is excessive activity of proteases, and an imbalance between proteases and endogenous antiproteases. Corticosteroids do not appear to have any effect on the inflammation in COPD, with no changes in neutrophilic inflammation, reduction in inflammatory mediators, or proteases. There is a contrasting effect of corticosteroids on granulocytes, with a reduction in eosinophil survival but a prolongation of neutrophil survival. This is consistent with a failure of long-term corticosteroids to alter the progression of COPD, and indicates that new types of anti-inflammatory treatment need to be developed in the future.

Potential causes of pulmonary hypertension in COPD include emphysematous destruction of the capillary bed, remodeling of pulmonary vessels and hypoxic pulmonary vasoconstriction. In pulmonary arteries of subjects with COPD, thickening of the intimal layer is the most consistent morphological change produced by the proliferation of smooth muscle cells and the deposition of both elastic and collagen fibers.

Hypoxaemia is the principal factor determining endothelial dysfunction which leads to vasoconstriction. However endothelial dysfunction and intimal thickening may be present also in smokers with mild COPD who are not hypoxemic, indicating that factors other than hypoxemia, might be capable of producing vascular changes in smokers. The recent observation of an infiltration of inflammatory cells, mainly CD8+ T lymphocytes, in the adventitia of pulmonary arteries in smokers with COPD supports a possible role of these cells in inducing vascular alterations.

COPD is progressive and sometimes irreversible; there is currently no cure. The clinical development of COPD is typically described in three stages, as defined by the Global Initiative for Chronic Obstructive Lung Disease (GOLD):

GOLD 0: Lung function is normal. At risk. Chronic symptoms (cough, sputum).

GOLD I Mild: FEV1/FVC<70%, FEV1≧80% of predicted value. With or without chronic symptoms (cough, sputum).

GOLD II Moderate: FEV1/FVC<70%, 50%≦FEV1<80% PW. With or without chronic symptoms (cough, sputum).

GOLD III Severe: FEV1/FVC<70%, 30%≦FEV1<50% PW. With or without chronic symptoms (cough, sputum).

GOLD IV Very severe: FEV1/FVC<70%, FEV1<30% PW or FEV1<50% PW with chronic respiratory failure.

COPD prevalence increases with age, but there is a dramatic synergy with smoking such that smokers have higher COPD prevalence and mortality and lung function losses. A smoker is 10 times more likely than a non-smoker to die of COPD. When inhaled, the smoke paralyzes the microscopic hairs (cilia) lining the bronchial tree. Irritants and infectious agents caught in the mucus remain in the bronchial tree rather than being swept out by the cilia. This can inflame bronchial membranes, eventually resulting in chronic obstruction. Other indoor and outdoor air pollutants may damage the lungs and contribute to COPD.

Although there is no cure for COPD, medications that are prescribed for people with COPD include:

Fast-acting beta 2-agonists, such as salbutamol which can help to open narrowed airways;

Anticholinergic bronchodilators, such as ipratropium bromide, and theophylline derivatives, all of which help to open narrowed airways;

Long-acting bronchodilators, which help relieve constriction of the airways and help to prevent bronchospasm associated with COPD;

Inhaled or oral corticosteroids, that help reduce inflammation;

Antibiotics that are often given at the first sign of a respiratory infection to prevent further damage and infection in diseased lungs;

Expectorants that help loosen and expel mucus secretions from the airways, and may help make breathing easier;

Lung transplantation is being performed in increasing numbers and may be an option for people who suffer from severe emphysema;

Lung volume reduction surgery, shows promise and is being performed with increasing frequency;

Special treatments for al-antitrypsin (AAT) deficiency emphysema include AAT replacement therapy (a life-long process) are being evaluated;

Current research into COPD is also focusing on gene therapy to substitute for the AAT deficiency.

Newer developments describe the successful use of vasoactive intestinal peptide (VIP) and pituitary adenylate cyclase-activating polypeptide (PACAP) in the treatment of COPD (WO 03/61680)

Cystic Fibrosis (CF)

Chronic lung disease is the chief cause of morbidity and mortality in CF. Bacterial colonization of the airways generally occurs within the first year or two after birth. Patients with CF have a predisposition to subsequent chronic colonization and infection with *Pseudomonas aeruginosa*, an organism whose presence in the CF lung is associated with progressive respiratory compromise. Infection is associated with an exuberant inflammatory response dominated by neutrophils and the potent inflammatory mediators that are released by activated neutrophils. An inexorable decrease in pulmonary function is the norm, leading eventually to death or to a need for lung transplantation. The experimental focus on the function of the CF gene CFTR in regulating epithelial ion transport has provided a compelling account of the pathogenesis of gastrointestinal disease in CF, as well as of the genesis of such CF-associated phenomena as high sodium chloride content in sweat. However, the examination of altered ion and water transport alone has failed to elucidate the path from gene to pathogenesis in the CF lung, something that has hindered therapeutic advances.

Indeed, it is notable that airway surface fluid is now believed to have normal concentrations of chloride and sodium in patients with CF. Another long-held pathogenic dogma regarding inflammation and infection in CF has also become suspect. It had been assumed that ineffective clearance of bacteria from the CF airway was primary to pathogenesis, leading secondarily to destructive chronic airway inflammation. It now seems possible that the causality is backwards in that formulation. There is a growing consensus that the CF airway is marked by an aberrant, exaggerated proinflammatory propensity that predates infection. In vivo studies using fetal human tracheal xenografts strongly suggest that this basal proinflammatory predisposition of the CF airway leads to the development of mucosal damage after infection, damage that is itself integral to subsequent persistent bacterial colonization of the airway. The airway inflammatory response in CF is persistently neutrophilic, marked by upregulation of neutrophil chemotactic mediators such as interleukin 8 (IL-8) and leukotriene B4 (LTB4); florid accumulation of neutrophils in the airways; and neutrophil activation, with release of toxic products such as neutrophil elastase. The initial inflammatory response to most bacterial stimuli, in the lung and elsewhere, is "acute", that is, neutrophil dominant. However, in the absence of bacterial clearance there is normally modulation over time to less histotoxic, "chronic" inflammation, a shift marked by the presence and immunoregulatory to activity of monocytic cells and lymphocytes. An unusual feature of inflammation in the CF airway is that such modulation never takes place.

Pulmonary Arterial Hypertension, Primary Pulmonary Hypertension and Secondary Pulmonary Hypertension and Arterial Hypertension Pulmonary arterial hypertension (PAH) is a fatal disease causing progressive right heart failure within three years after diagnosis. Recently, various pathophysiological changes associated with this disorder, including vasoconstriction, vascular remodelling (i.e. proliferation of both media and intima of the pulmonary resistance vessels), and in situ thrombosis have been characterized. Impairment of vascular and endothelial homeostasis is evidenced from a reduced synthesis of prostacyclin ($PGI_2$), increased thromboxane production, decreased formation of nitric oxide and increased synthesis of endothelin. The intracellular free calcium concentration of VSMC of pulmonary arteries in PAH has been reported to be elevated.

Comparable to the pulmonary circulation, endothelial cells of the systemic circulation release both relaxing and contracting factors that modulate vascular smooth muscle tone and also participate in the pathophysiology of essential hypertension. Endothelium-dependent vasodilation is regulated primarily by nitric oxide but also by an unidentified endothelium-derived hyperpolarizing factor and by prostacyclin. Endothelium-derived contracting factors include endothelin-I, vasoconstrictor prostanoids, angiotensin II and superoxide anions. Under physiological conditions, there is a balanced release of relaxing and contracting factors. The balance can be altered in cardiovascular diseases such as hypertension, atherosclerosis, diabetes and other conditions, thereby contributing to further progression of vascular and end-organ damage. In particular, endothelial dysfunction leading to decreased bioavailability of nitric oxide impairs endothelium-dependent vasodilation in patients with essential hypertension and may also be a determinant for the premature development of atherosclerosis.

The therapy of pulmonary and arterial hypertension is unsatisfactory. Current therapy involves calcium cannel blockers and prostacyclins. Newer developments describe the application of vasoactive intestinal peptide (VIP) and pituitary adenylate cyclase-activating polypeptide (PACAP) in treatment of PPH, SPH and arterial hypertension. (see WO 02/43746).

Bronchiolitis Obliterans (BO)

Bronchiolitis obliterans is a chronic inflammatory disease characterised by a process centred in and around membranous and/or respiratory bronchioles with sparing of a considerable portion of the other parenchymal structures.

Bronchiolitis obliterans is a disease with airflow limitation that is not fully reversible.

The airflow limitation is usually progressive and is associated with an abnormal inflammatory response of the lungs. The prognosis is worse.

Bronchiolitis obliterans, the chronic rejection following lung transplantation, is an important factor limiting long term survival in lung graft recipients. As this chronic rejection responds only poorly to immunosuppression, re-transplantation remains the ultimate choice for patients with progressive disease. It is known from experimental and clinical studies that the T-helper (Th) 1 and the Th17 response play a critical role in the pathogenesis of BO. Thus, novel therapeutic strategies that target these immunologic reactions could be promising in the setting of BO. Vasoactive intestinal peptide (VIP) is a Th2 cytokine with anti-inflammatory properties, while Interferon (IFN)-γ is a Th1 cytokine with antifibrotic activity that inhibits the IL-17 production by Th17 cells. In the proposed project VIP and IFN-y will be used as a single or combination treatment to prevent BO development in an experimental model of orthotopic rat lung transplantation. The aim of this preclinical study is to study whether VIP or IFN-γ are effective in prevention/improvement of BO in the experimental model and thus could be introduced into clinical trials. Moreover, the aim of this study is to investigate the mechanisms of action of the proposed therapeutics, including the role of VIP in inducing regulatory T cells following transplantation and the role of IFN-γ in inhibiting inflammation promoted by IL-17.

Vasoactive Intestinal Peptide (VIP):

VIP is a 28 amino acid naturally occurring human peptide consisting of the following amino acid sequence (from N- to C-terminal):

```
                                        (SEQ ID No. 1)
His-Ser-Asp-Ala-Val-Phe-Thr-Asp-Asn-Tyr-Thr-Arg-

Leu-Arg-Lys-Gln-Met-Ala-Val-Lys-Lys-Tyr-Leu-Asn-

Ser-Ile-Leu-Asn
```

The peptide is synthesized in various components of the central nervous system, e.g. specific brain regions like hippocampus and cortex as well as in the pituitary gland and peripheral ganglia. VIP is furthermore secreted by immune cells and by some neoplastic cells (e.g. pancreatic cancer). Healthy individuals exhibit low concentration of VIP (<40 pg/ml serum).

VIP is a widely distributed peptide hormone that mediates a variety of physiological responses including gastrointestinal secretion, relaxation of gastrointestinal vascular and respiratory smooth muscle, lipolysis in adipocytes, pituitary hormone secretion, and excitation and hyperthermia after injection into the central nervous system. Under physiologic conditions VIP acts as a neuroendocrine mediator. Importantly, VIP is a potent anti-inflammatory agent, as treatment with VIP significantly reduced incidence and severity of arthritis in an experimental model, completely abrogating joint swelling and destruction of cartilage and bone. VIP may elicit different biological and/or therapeutic effects some of them are described in WO 9106565, EP 0536741, U.S. Pat. No. 3,880,826, EP 0204447, EP 0405242, WO 9527496, EP 0463450, EP 0613904, EP 0663406, WO 9735561, and EP 0620008.

VIP receptor has been detected on airway epithelium of the trachea and the bronchioles. It is also expressed in macrophages surrounding capillaries, in connective tissue of trachea and bronchi, in alveolar walls, and in the subintima of pulmonary veins and pulmonary arteries.

As mentioned, VIP has a strong bronchorelaxing, vasorelaxing and anti-inflammatory effect. Therefore inhalation of VIP (or receptor selective analogous) is a promising approach for lung diseases. Although VIP in principal have been successfully used in clinical trials for the treatment of PPH, COPD and CF recently, these compounds unfortunately underlie considerable enzymatic degradation in bronchial tissue, especially when they are administered via inhalation.

Therefore, there is a need to provide peptides having these biological activities of VIP, which show, however, improved properties, especially in context with enhanced stability and enhanced therapeutic efficacy.

SUMMARY OF THE INVENTION

It has been shown that novel synthetic peptides derived from the original structure of wild-type VIP are effective in the preclinical test in vitro.

The biological and therapeutic efficacy and effectiveness of the new synthetic peptides is increased as compared to the efficacy and effectiveness of VIP. Moreover, the novel peptides show an increased stability in pharmaceutical composition, formulation and an enhanced serum half-life in comparison to VIP.

Therefore, it is object of the present invention to provide these novel compounds, which maybe are useful for the prevention and/or treatment of COPD, CF, BO, PAH, SPH and other lung/bronchi related diseases, and therapeutic methods, wherein said compounds are used.

The novel peptides according to the invention are selected from the group consisting of (amino acids 1-28 from N- to C-terminal):

```
                                    (SEQ ID No.: 2 (A-15))
His (Ac)-Ser-Asp-Ala-Val-Phe-Thr-Asp-Asn-Tyr-Thr-

Arg-Leu-Arg-Lys-Gln-Met (O)-Ala-Val-Lys-Lys-Tyr-

Leu-Asn-Ser-Ile-Leu-Asn (SEQ ID No.: 3 (A-18))
His (Ac)-Ser-Asp-Ala-Val-Phe-Thr-Asp-Asn-Tyr-Thr-

Arg-Leu-Arg-Lys-Gln-Met-Ala-Val-Lys-Lys-Tyr-Leu-

Asn-Ser-Val-Leu-Asn (SEQ ID No.: 4 (A-20))
His (Ac)-Ser-Asp-Ala-Val-Phe-Thr-Asp-Asn-Tyr-Thr-

Arg-Leu-Arg-Lys-Gln-Met (O)-Ala-Val-Lys-Lys-Tyr-

Leu-Asn-Ser-Val-Leu-Asn
```

Herein, His(Ac) (position 1) means N-acetyl histidine, and Met(O) (position 17) means methionine oxide. The underlined amino acid residues differ from the corresponding amino acid residues in the VIP sequence (SEQ ID No. 1).

Surprisingly, said compounds are mostly distinctly more effective and active than VIP or PACAP under identical preclinical/physiological conditions.

It could be shown by the inventors that the enhanced efficacy versus VIP can be achieved by replacing the histidine residue at position 1 with acetyl-histidine (His(Ac)) and/or by replacing the methionine residue (Met) at position 17 with methionine oxide (Met(O)). Substitution with His(Ac) and Met(O) is preferred.

In addition, the peptides according to the invention show improved anti-inflammatory (FIGS. 5a,b; 6a,b; 8; 10a,b; 11a,b; 12a,b), antiproliferative (FIG. 13) bronchodilatory and vasodilatory properties (FIGS. 4; 7; 9) as compared to VIP.

For example, by administering the peptide of SEQ ID No. 2 (A-15) or SEQ ID No. 4 (A-20) the lung functions of a patient can be improved by 10-20% as compared to the administration of VIP (SEQ ID No.: 1) under equal conditions in COPD or CF, in case of the peptide of SEQ ID No. 3 by 10-15%.

Surprisingly, said compounds are mostly more stable under identical or comparable conditions in vivo and in vitro, thus increasing serum-half life, and/or under in vitro conditions as compared to VIP or PACAP. It could be shown by the inventors that the improvement in stability can be achieved by replacing the native amino acid residue Ile at position 26 of VIP with Val or Ala, preferably Val. This amino acid substitution leads to an increase of stability, for example, in physiological solutions of about 100%. Also in vivo serum-half life in a patient can be enhanced as compared to VIP administration by 20-100%, preferably between 50-80%.

Furthermore, it could be shown according to the results of the invention that enzymatic degradation of VIP or PACAP, which easily occurs in the lungs and bronchi, can be improved by the peptides according to the invention, wherein the modification of VIP resulting in said novel peptides does not impair the biological functions of the obtained peptides. Thus, the novel peptides are preferably suitable for inhalation. In a preferred embodiment of the invention the novel peptides can be administered to the patient by inhalation by means of nanobeads or nanoparticles in a more effective manner than VIP.

The said compounds maybe are highly active in patients preferably suffering from COPD, CF or BO, and also COPD, which is preferably not accompanied by lung hypertension (such as primary or secondary pulmonary hypertension (PPH, SPH)).

The synthetic peptides according to the invention maybe are furthermore suitable for the prophylaxis and treatment of smoker's cough and similar symptoms.

Generally, the lung functions in a patient suffering from any of the lung diseases as specified above, preferably, COPD, CF or BO can be improved by 10-35%, preferably 10-20%, more preferably 15-25% and most preferably 20-30% as compared to the treatment with VIP under identical conditions. Thus in COPD related diseases the FEV1 value can be increased depending on the stage of disease by 10-50% compared to VIP. Since VIP itself may improve the FEV1 value by 5-50% as compared to non-treated COPD patients, the favorable impact of the novel peptides according to the invention is remarkable.

In summary, it is an object of this invention to provide the following topics:

A synthetic peptide having the biological activity of vasoactive intestinal peptide (VIP), wherein said peptide has improved properties than VIP, said peptide is selected from the group consisting of:

(SEQ ID No.: 2)
(i) His (Ac)-Ser-Asp-Ala-Val-Phe-Thr-Asp-Asn-Tyr-

Thr-Arg-Leu-Arg-Lys-Gln-Met (O)-Ala-Val-Lys-Lys-

Tyr-Leu-Asn-Ser-Ile-Leu-Asn, (SEQ ID No.: 3)
(ii) His (Ac)-Ser-Asp-Ala-Val-Phe-Thr-Asp-Asn-Tyr-

Thr-Arg-Leu-Arg-Lys-Gln-Met-Ala-Val-Lys-Lys-Tyr-

Leu-Asn-Ser-Val-Leu-Asn,
and (SEQ ID No.: 4)
(iii) His (Ac)-Ser-Asp-Ala-Val-Phe-Thr-Asp-Asn- Tyr-Thr-Arg-Leu-Arg-Lys-Gln-Met (O)-Ala-Val-Lys- Lys-Tyr-Leu-Asn-Ser-Val-Leu-Asn, wherein His(Ac) means N-acetyl histidine, and Met(O) means methionine oxide.

A corresponding synthetic peptide comprising the peptide of SEQ ID No. 2:

His(Ac)-Ser-Asp-Ala-Val-Phe-Thr-Asp-Asn-Tyr-Thr-

Arg-Leu-Arg-Lys-Gln-Met(O)-Ala-Val-Lys-Lys-Tyr-

Leu-Asn-Ser-Ile-Leu-Asn.

A corresponding synthetic peptide comprising the peptide of SEQ ID No. 3:

His(Ac)-Ser-Asp-Ala-Val-Phe-Thr-Asp-Asn-Tyr-Thr-

Arg-Leu-Arg-Lys-Gln-Met-Ala-Val-Lys-Lys-Tyr-Leu-

Asn-Ser-Val-Leu-Asn.

A corresponding synthetic peptide comprising the peptide of SEQ ID No. 4:

His(Ac)-Ser-Asp-Ala-Val-Phe-Thr-Asp-Asn-Tyr-Thr-

Arg-Leu-Arg-Lys-Gln-Met(O)-Ala-Val-Lys-Lys-Tyr-

Leu-Asn-Ser-Val-Leu-Asn.

A pharmaceutical composition comprising a corresponding synthetic peptide according as specified, optionally together with a pharmaceutically acceptable carrier, excipient or diluent.

A corresponding pharmaceutical composition, wherein said synthetic peptide is coupled to a nanoparticle or nanobead, or is encapsulated by nanoparticles or nanobeads.

A corresponding pharmaceutical composition, wherein said synthetic peptide is formulated as aerosol.

A corresponding pharmaceutical composition, wherein said peptides or polypeptides are present in a concentration range between 3 and 3000 mg/L, preferably 10-500 mg/L A Use of a peptide or a pharmaceutical composition as specified for the manufacture of a medicament for the treatment of a patient suffering from lung or bronchi diseases or diseases which are related to lung or bronchi diseases.

The corresponding use, wherein said disease is chronic obstructive pulmonary disease (COPD).

The corresponding use, wherein said COPD is functionally uncoupled from or pharmacologically not correlated to hypertension diseases.

The corresponding use, wherein said disease is cystic fibrosis (CF).

The corresponding use, wherein said disease is bronchiolitis obliterans (BO).

The corresponding use, wherein the administration of the synthetic peptide or said pharmaceutical composition leads to an improvement of lung functions in the patient between 20-30% related to the administration with VIP under equal conditions.

The corresponding use, wherein the administration of the synthetic peptide or said pharmaceutical composition leads to an increased serum half-life in the patient as compared to VIP.

The corresponding use, wherein said peptide is provided into the lung of the patient by inhalation.

SHORT DESCRIPTION OF THE FIGURES AND TABLES

Table 1: The table 1 shows the Consort E-Flowchart of the clinical study.

Table 2: The table 2 shows the physical component summary (PCS) measures and mental component summary (MCS) measures. The variables were calculated as the change from baseline to the endpoint.

Table 3: The table 3 shows the adverse events of the clinical study.

Table 4: The table 4 shows the lung function of CF patient for and after 3 months VIP treatment.

Table 5: The table 5 shows the nitrite production by monocytes after LPS stimulation by SEQ ID No.:1 (VIP) and SEQ ID No.:2 (A-15), SEQ ID No.:3 (A-18) and SEQ ID No.:4 (A-20).

Table 6: The table 6 shows the cAMP production after SEQ ID No.:1 (VIP) (table 6a), SEQ ID No.:2 (A-15) (table 6b) and SEQ ID No.:3 (A-18) (table 6c) stimulation.

FIG. 1 depicts the SEQ ID No.:1 (VIP) serum concentration in serum from normal subjects and patients with COPD and pancreatic cancer.

FIG. 2: Mean Forced Expiratory Volume in one Second (FEV1) at Selected Times (A). The numbers at each time point refer to data derived from VIP (■) or placebo (○) treatment groups; asterixs denote P<0.01 for the comparison with placebo. Median Change in Inspiratory Volume Capacity (B) as Compared to the Value at Randomisation (Day 0) in the Placebo (○) or VIP group (■). Asterixs denote P<0.01 for comparison with placebo.

DETAILED DESCRIPTION

Figure 1:
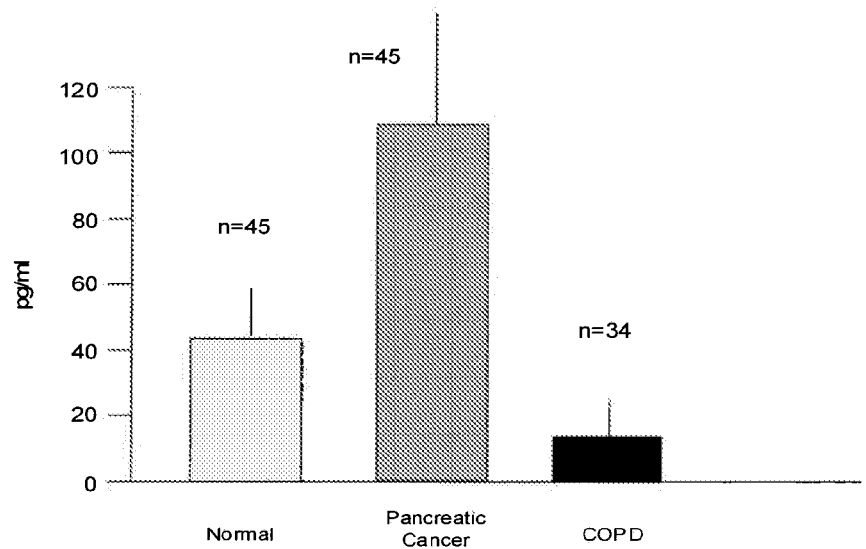

The term "same biological activity" means the biological, physiological or therapeutic activity or functionality compared with the relevant properties of said peptides and polypeptides, preferably VIP or PACAP.

The term "derivative or analogue" means a peptide compound which is derived more or less directly from the corresponding peptide, such as VIP or PACAP as such, and is altered by some additions, deletions, mutations or modifications without altering the biological properties of the parent peptide. Suitable VIP derivatives are, for example, disclosed in WO 8905857, WO 9106565, EP 0663406 and WO 9729126 (Fmoc protected VIP). The term includes also conjugates of peptides and polypeptides according to the invention that consist of the parent peptide or polypeptide coupled to lipophilic entities, such as liposomes. VIP—liposome products are, for example, disclosed in WO 9527496 or WO 9735561, and have improved properties with respect to bioavailability and proteolytic degradation. Furthermore, the term includes also fragments, slightly modified fragments including truncated forms.

The term "stabilized form" means a derivative or analogue of the peptides according to the invention, wherein the parent peptide was altered in order get more stability and increased half-life in blood and serum. Such stabilized forms are preferred if the polypeptide is fragmented by enzyme activity. Possible stabilized forms are cyclic peptides, fusion proteins, preferably Fc-fusion proteins or pegylated peptides, for example pegylated VIP or pegylated peptides according to the invention. The addition of polyethylene glycol increases stability of the peptides and polypeptides of this invention at physiological pH as compared to non-pegylated compounds. The pegylated polypeptide/protein is also stabilized with regard to salts.

The term "fusion protein" means a compound, especially a stabilized form, consisting of a peptide according to the invention, which is fused to another peptide polypeptide or protein. Such a protein is preferably an immunoglobulin molecule, more preferably a fragment thereof, most preferably a Fc portion of an IgG molecule, preferably an IgG1. A Fc-VIP fusion protein is described in WO 200024278 and shows an improved half-life in serum and blood. Fc fusions according to invention are Fc-peptide SEQ ID No.2 and Fc-peptide SEQ Id. No 3, and Fc-peptide SEQ ID No. 4, wherein preferably the peptide is fused to the C-terminal of the Fc portion of the immunoglobulin.

The term "individual or patient" preferably refers to mammals, especially is humans. The compound is used in a pharmaceutical composition and formulations, comprising, as a rule, a pharmaceutically acceptable carrier, excipient or diluents. Techniques for the formulation and administration of the compounds of the present invention may be found in "Remington's Pharmaceutical Sciences" Mack Publishing Co., Easton Pa.

The term "synthetic peptide" comprises according to the understanding of the invention peptides, which consist of natural amino acids and partially of chemically modified natural amino acid residues, and have been produced either completely by chemical synthesis, or by recombinant methods in combination with chemical modification of single amino acid residues. In case of the novel peptides according to the invention, which consist of 28 amino acid residues, a standard peptide synthesis is preferred.

As used herein, the term "pharmaceutically acceptable carrier" means an inert, non toxic solid or liquid filler, diluent or encapsulating material, not reacting adversely with the active compound or with the patient, or any other formulation such as tablets, pills, dragees, capsules, gels, syrups, slurries, suspensions and the like. Suitable, preferably liquid carriers are well known in the art such as sterile water, saline, aqueous dextrose, sugar solutions, ethanol, glycols and oils, including those of petroleum, animal, vegetable, or synthetic origin, for example, peanut oil, soybean oil and mineral oil. The formulations according to the invention may be administered as unit doses containing conventional non-toxic pharmaceutically acceptable carriers, diluents, adjuvants and vehicles that are typical for parenteral administration.

Unit doses according to the invention may contain daily required amounts of the compound according to the invention, or sub-multiples thereof to make up the desired dose.

The optimum therapeutically acceptable dosage and dose rate for a given patient (mammals, including humans) depends on a variety of factors, such as the activity of the specific active material employed, the age, body weight, general health, sex, diet, time and route of administration, rate of clearance, enzyme activity, the object of the treatment, i.e., therapy or prophylaxis and the nature of the disease to be treated. Therefore, in compositions and combinations in a treated patient (in vivo) a pharmaceutical effective daily dose of the peptide of this invention is between about 5 ng and 200 µg/kg body weight, preferably between 20 ng and 20 µg/kg body weight.

The preferred administration of the peptides according to this invention is the inhalation of aqueous solutions containing a peptide of the invention. The aqueous solution is preferably an isotonic saline solution (NaCl) which can contain additional drugs or other suitable ingredients. Preferably, the peptide compounds are used in said solutions in a stabilized form as specified above. Especially preferred solutions are isotonic NaCl solutions containing the peptide in a pegylated form. The concentration of the peptide used in therapy in said solutions vary according to the invention between 10 mg and 300 mg/L solution, preferably between 30 mg and 100 mg/L. If stabilized forms, such as pegylated forms of the peptides of the invention as specified above, are used the concentration as well as the over-all dosage of the selected peptide of the invention can decreased, as a rule. The inhalation of the peptides according to the invention can be carried out, as a rule, 1-4 times a day for 5-45 minutes, preferably 10-20 minutes, according to the severity of the disease and the efficacy of the compounds used for the treatment.

For inhalations the compound according to the invention is preferably brought in an aerosol form. Aerosols and techniques to make them are well known in the art. Aerosols applicable by inhalers containing a peptide of the invention are preferred especially in the case of COPD. Administration by nasal spray techniques are also suitable.

Administration of the synthetic peptides according to the invention, includes also nanoparticles or nanobeads to which the peptides according to the invention are linked or coupled chemically or by van-der Waals forces, or in which said peptides are encapsulated. Nanoparticles or -beads are naturally derived or synthetic mostly spherical particles with a diameter of <1000 nm, preferably <500 nm, more preferably <200 nm. The peptide delivery to the target cells can be improved by release out of inhaled nanobeads comprising a peptide according to the invention: the peptide is less likely to become degraded after a bolus delivery while all cell receptors are fully loaded, and the peptide can be protected by nano-beads, produced out of other enzyme substrates which, as mentioned above, competitively inhibits the enzymatic degradation of the therapeutic peptide. According to the invention nanobeads as carrier to deliver peptides deep into the lung by inhalation by, for example, ultrasonic nebulising, which produce a drop size of about 1-5, preferably 3 µm. Hence, each microdroplet carries many nanobeads loaded with the therapeutic novel peptide according to the invention. Suitable nanobeads are well known in the art, such as lipoparticles (liposomes), protamin (already known from insulin depot therapy), poly(D,L-lactic-co-glycolic) acid (PLGA), Thiolate or other polymeric carrier substrates. A comprehensive overview presenting nanoparticles suitable for drug delivery systems, which can be applied to the current invention, can be taken, for example, from J Pharm Pharmaceut Sci, 2000, 3(2), 234-258.

Therapeutically effective doses of the peptides according to the invention or their pharmaceutical compositions may be administered alone or as adjunctive therapy in combination with other pharmaceutically effective compounds, such as compounds with other drugs, e.g. fast-acting beta2-agonists (such as albuterol), anticholinergic bronchodilators (such as ipratropium bromide), long-acting bronchodilators, inhaled or oral corticosteroids, antibiotics, or antiproliferative compounds, e.g. D-24851, imatinib mesylate, or guanylhydrazone CNI-1493.

EXAMPLES

Example 1

VIP and COPD: Phase II, Double-Blind, Randomized, Placebo-Controlled Clinical Trial Chronic obstructive pulmonary disease (COPD) is characterised by progressive airflow limitation associated with chronic inflammation. Vasoactive intestinal peptide (VIP) is a potent bronchodilator, vasodilator and anti-inflammatory agent. The efficacy and safety of VIP in patients was assessed with moderate to severe COPD.

The present double-blind, randomized, placebo-controlled study was undertaken in an outpatient setting. COPD patients (n=34) were randomly assigned VIP 50 μg (n=17), or placebo (n=17), given per inhalation, 4 times daily for 12 weeks. VIP serum concentration was measured in all patients. Primary outcomes were health-related quality of life and exercise capacity. Secondary outcomes included the lung function parameters and COPD exacerbations.

Figure 2:
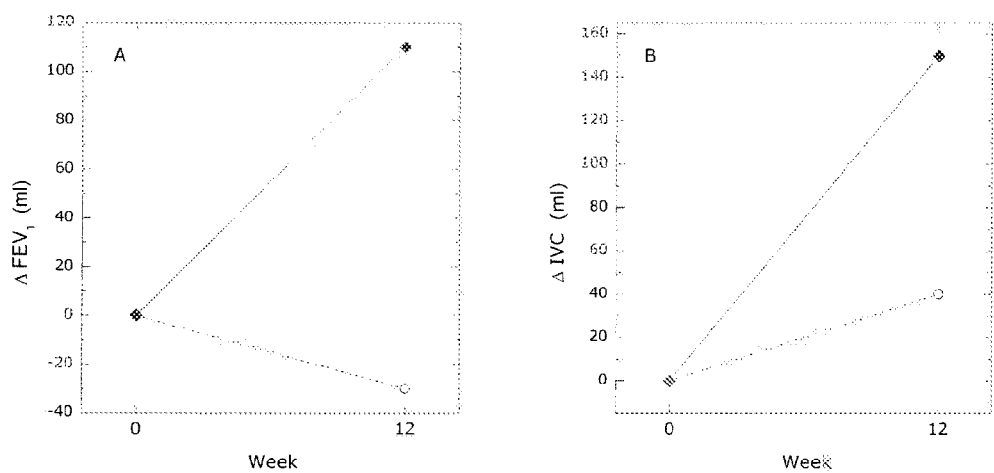
Figure 3:
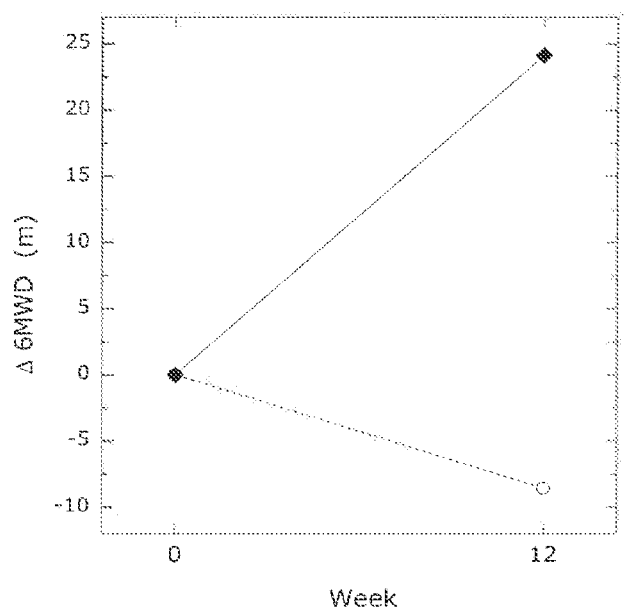
FIG. 3 depicts the Mean Change in Six-Minutes Walking Distance from Baseline to Day 90 in the VIP (■) and Placebo (○) Groups. P<0.01 for the comparison between VIP and placebo.
Figure 4:
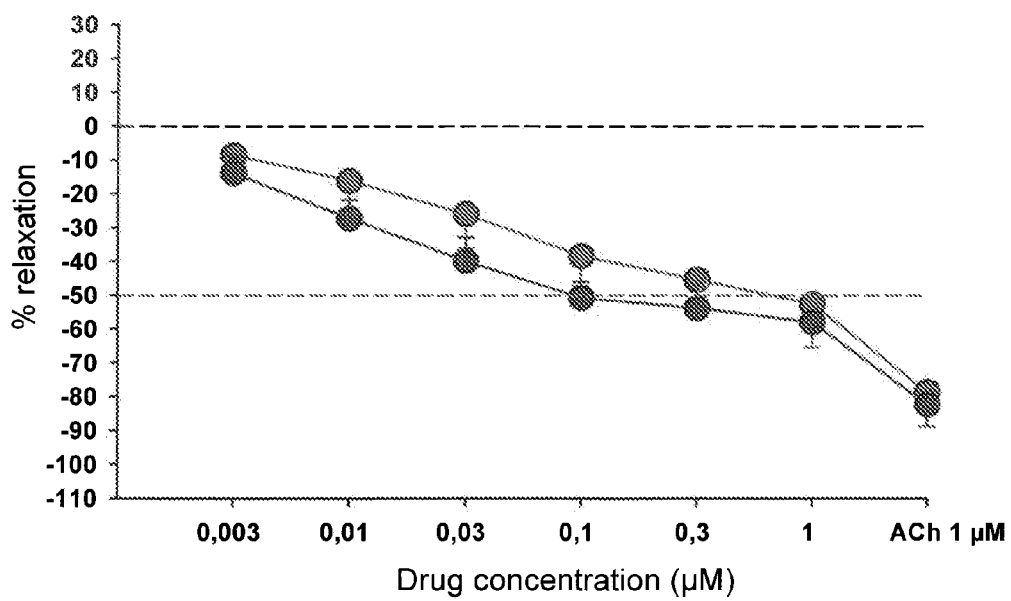
FIG. 4 depicts the effect of SEQ ID No.:1 (VIP) as compared to SEQ ID No.:2 (A-15) on the rat pulmonary artery in vitro experiments.
Figure 5A:
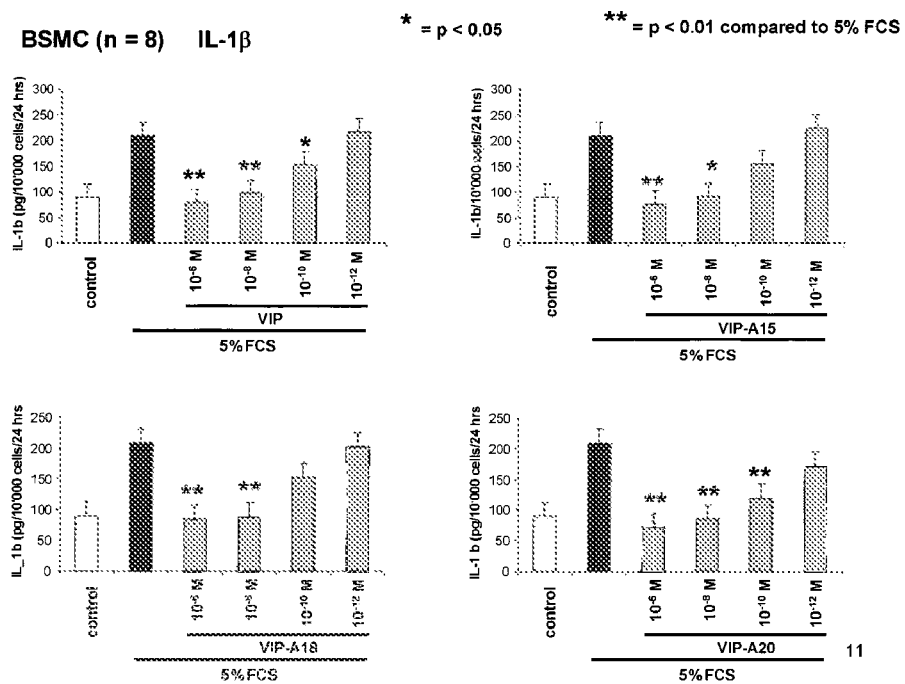
FIG. 5a depicts the effect of SEQ ID No.:1 (VIP) as compared to SEQ ID No.:2 (A-15), SEQ ID No.:3 (A-18) and SEQ ID No.:4 (A-20) on the Interleukin (IL)-1b production in bronchial smooth muscle cells (BSMC) in vitro.
Figure 5B:
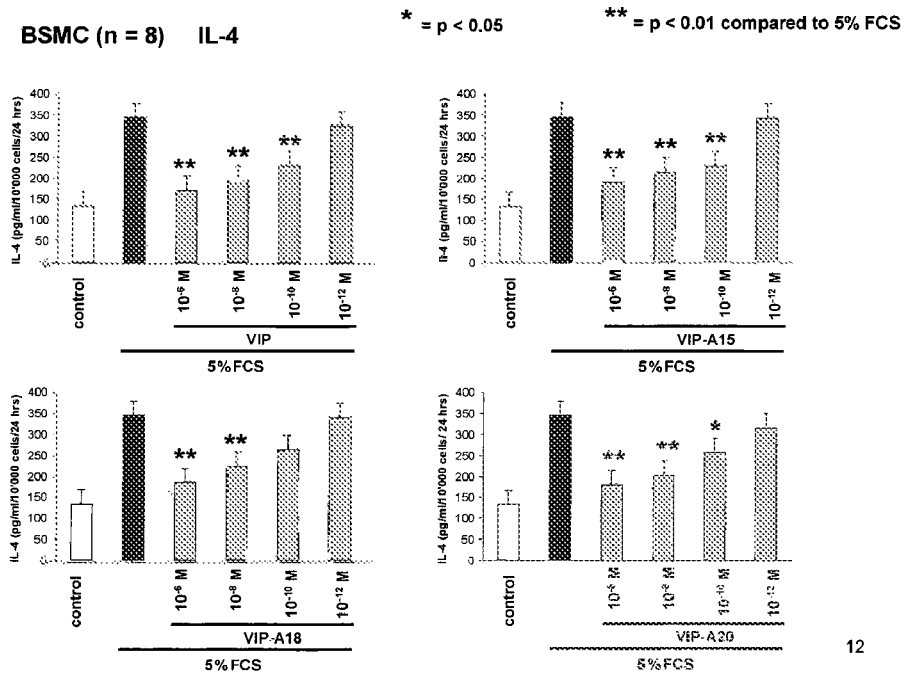
FIG. 5b depicts the effect of SEQ ID No.:1 (VIP) as compared to SEQ ID No.:2 (A-15), SEQ ID No.:3 (A-18) and SEQ ID No.:4 (A-20) on the Interleukin (IL)-4 production in bronchial smooth muscle cells (BSMC) in vitro.
Figure 6A:
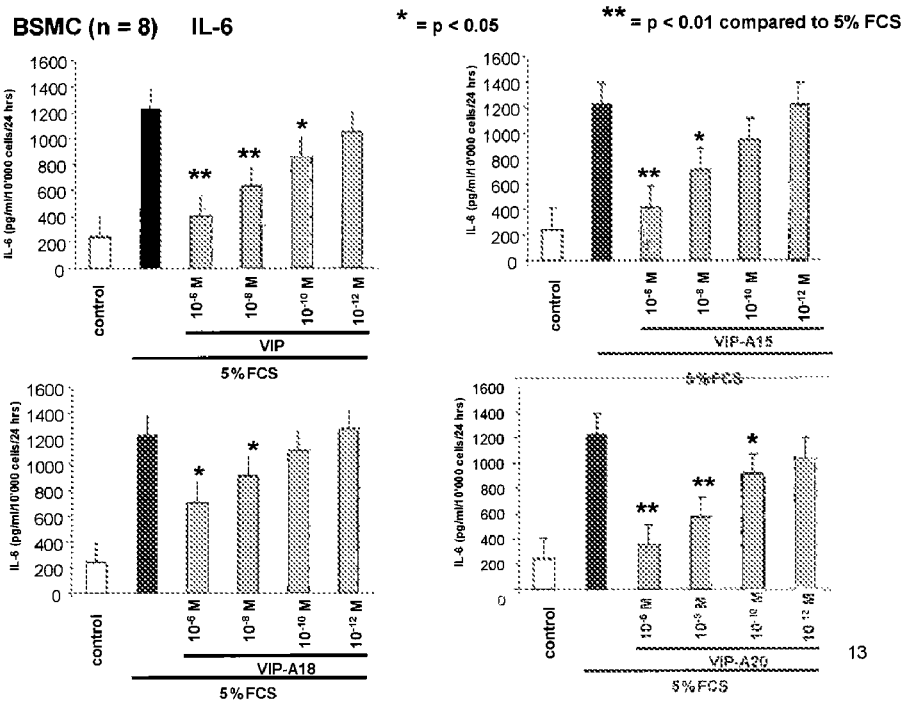
FIG. 6a depicts the effect of SEQ ID No.:1 (VIP) as compared to SEQ ID No.:2 (A-15), SEQ ID No.:3 (A-18) and SEQ ID No.:4 (A-20) on the Interleukin (IL)-6 production in bronchial smooth muscle cells (BSMC) in vitro.
Figure 6B:
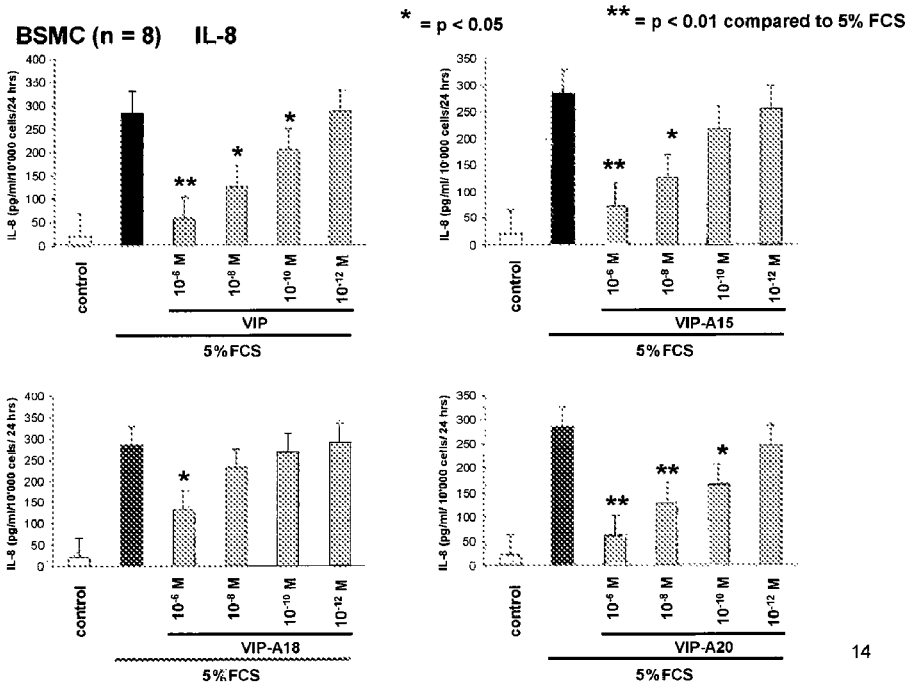
FIG. 6b depicts the effect of SEQ ID No.:1 (VIP) as compared to SEQ ID No.:2 (A-15), SEQ ID No.:3 (A-18) and SEQ ID No.:4 (A-20) on the Interleukin (IL)-8 production in bronchial smooth muscle cells in vitro.
Figure 7:
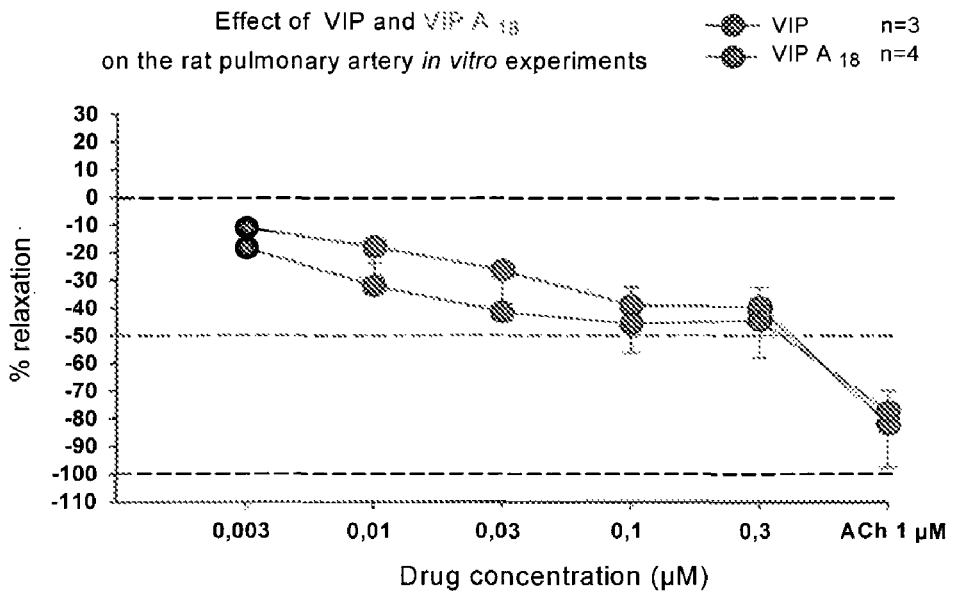
FIG. 7 depicts the effect of SEQ ID No.:1 (VIP) as compared to SEQ ID No.:3 (A-18) on the rat pulmonary artery in vitro experiments.
Figure 8:
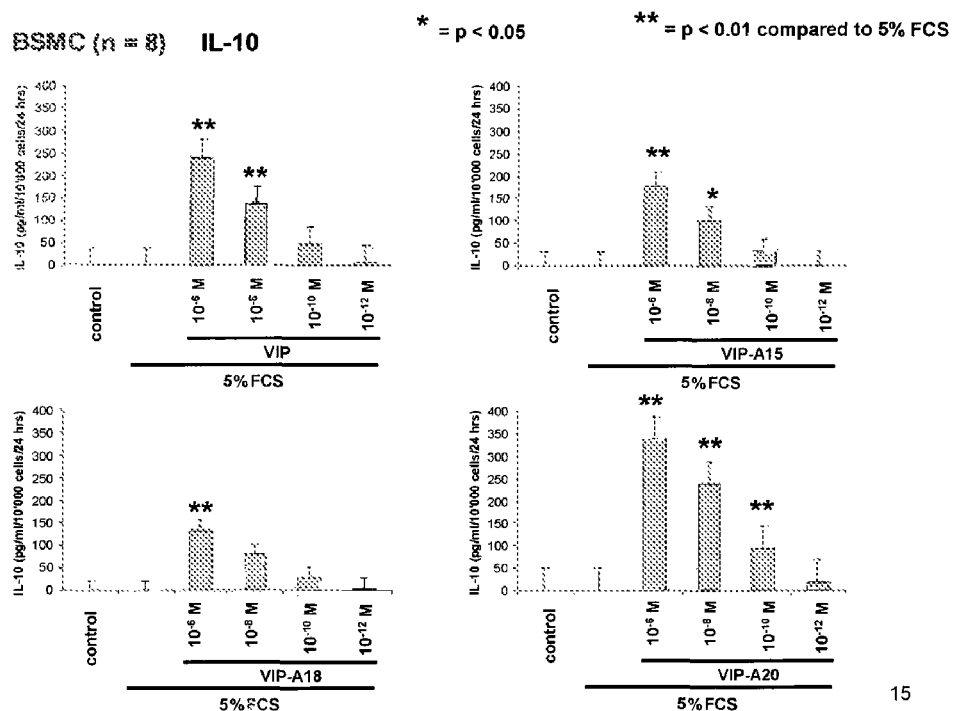
FIG. 8 depicts the effect of SEQ ID No.:1 (VIP) as compared to SEQ ID No.:2 (A-15), SEQ ID No.:3 (A-18) and SEQ ID No.:4 (A-20) on the Interleukin (IL)-10 production in bronchial smooth muscle cells in vitro.
Figure 9:
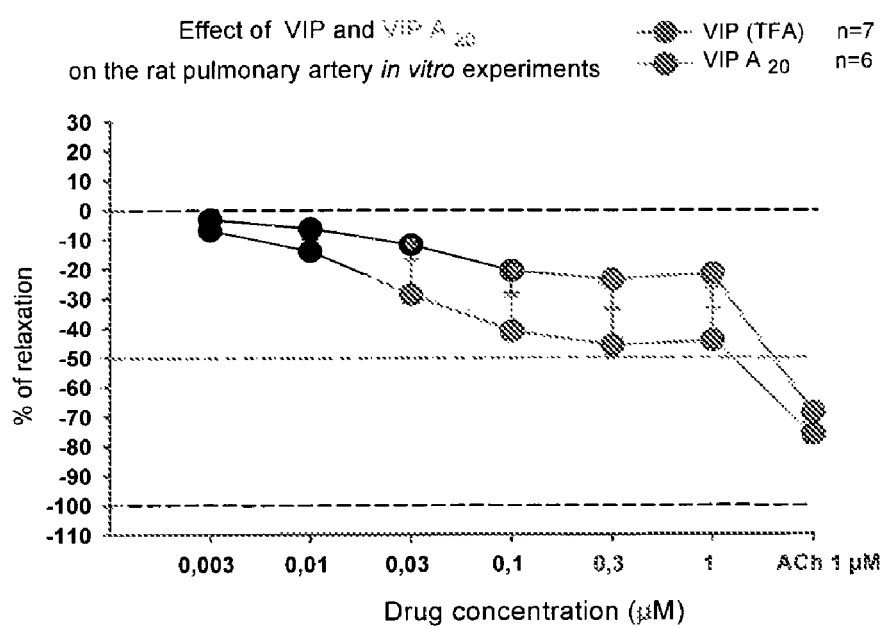
FIG. 9 depicts the effect of SEQ ID No.:1 (VIP) as compared to SEQ ID No.:4 (A-20) on the rat pulmonary artery in vitro experiments.
Figure 10A:
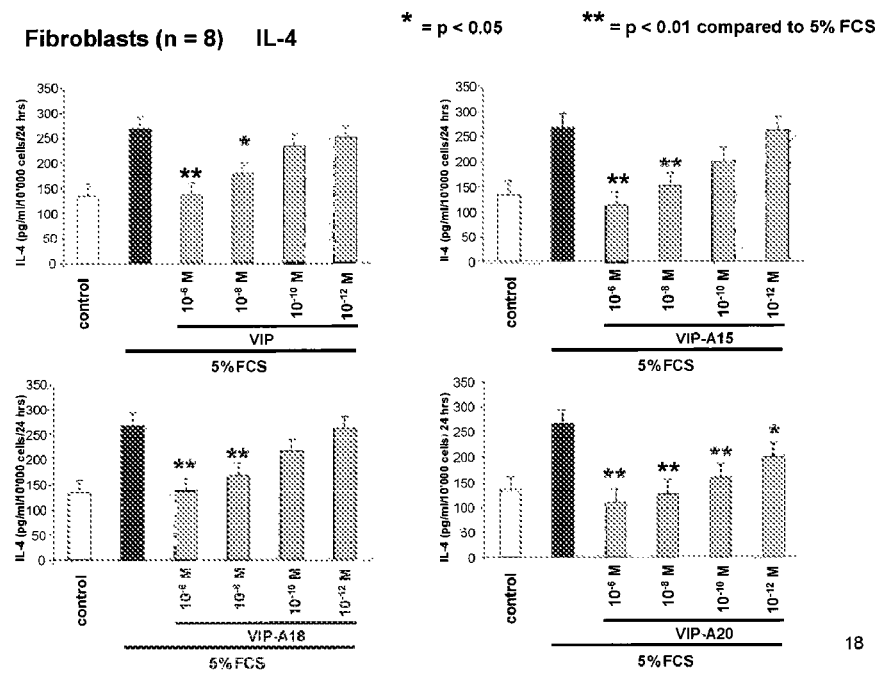
FIG. 10a depicts the effect of SEQ ID No.:1 (VIP) as compared to SEQ ID No.:2 (A-15), SEQ ID No.:3 (A-18) and SEQ ID No.:4 (A-20) on the Interleukin (IL)-4 production in fibroblasts in vitro.
Figure 10B:
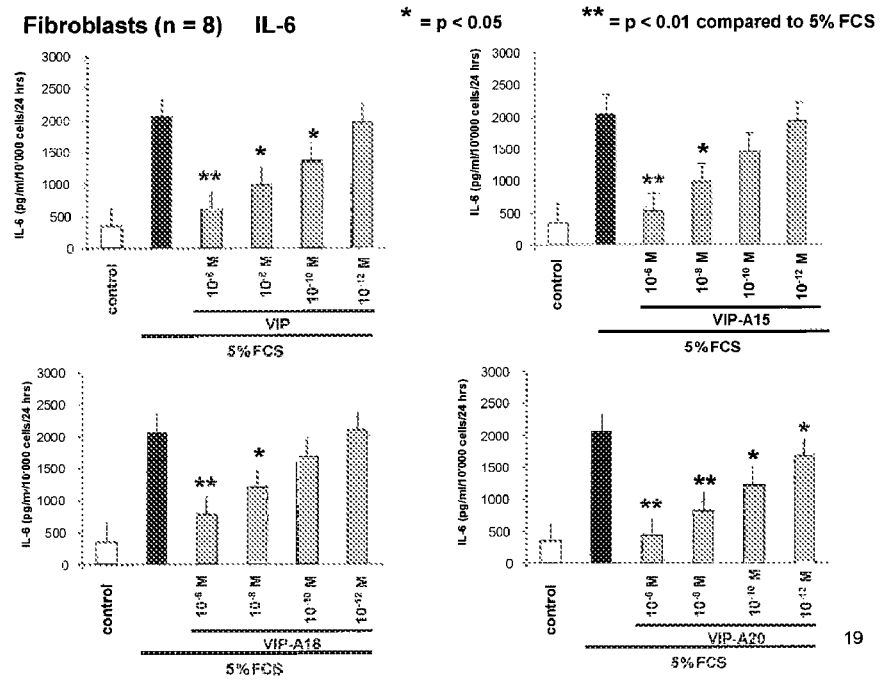
FIG. 10b depicts the effect of SEQ ID No.:1 (VIP) as compared to SEQ ID No.:2 (A-15), SEQ ID No.:3 (A-18) and SEQ ID No.:4 (A-20) on the Interleukin (IL)-6 production in fibroblasts in vitro.
Figure 11A:
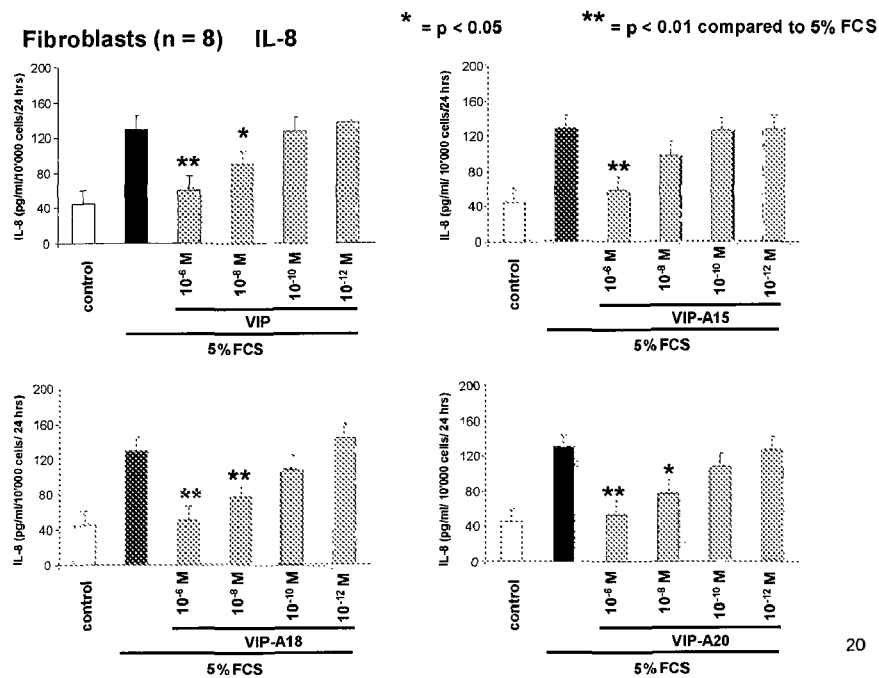
FIG. 11a depicts the effect of SEQ ID No.:1 (VIP) as compared to SEQ ID No.:2 (A-15), SEQ ID No.:3 (A-18) and SEQ ID No.:4 (A-20) on the Interleukin (IL)-8 production in fibroblasts in vitro.
Figure 11B:
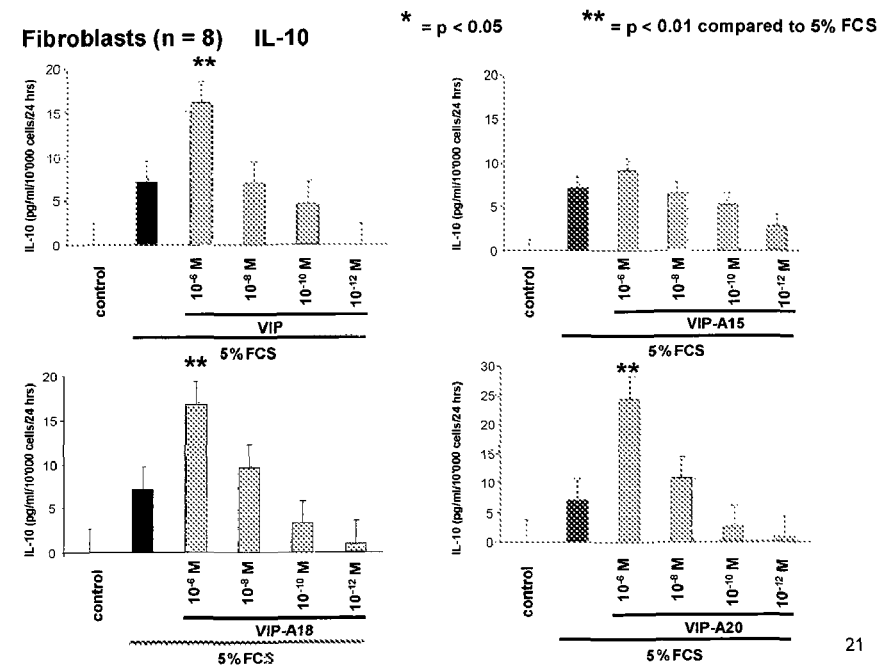
FIG. 11b depicts the effect of SEQ ID No.:1 (VIP) as compared to SEQ ID No.:2 (A-15), SEQ ID No.:3 (A-18) and SEQ ID No.:4 (A-20) on the Interleukin (IL)-10 production in fibroblasts in vitro.
Figure 12A:
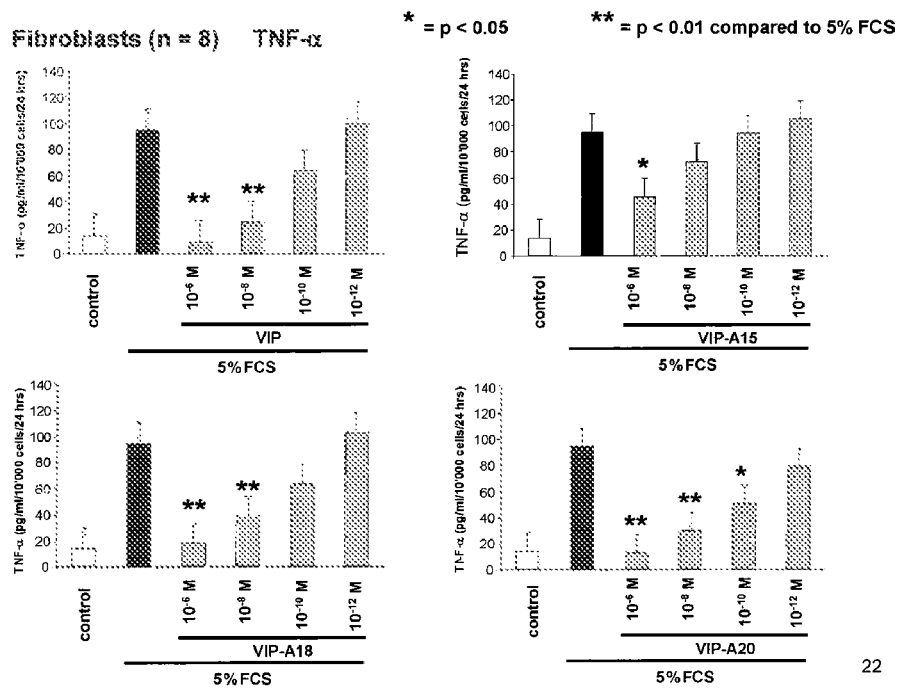
FIG. 12a depicts the effect of SEQ ID No.:1 (VIP) as compared to SEQ ID No.:2 (A-15), SEQ ID No.:3 (A-18) and SEQ ID No.:4 (A-20) on the tumor necrosis factor (TNF)-a production in fibroblasts in vitro.
Figure 12B:
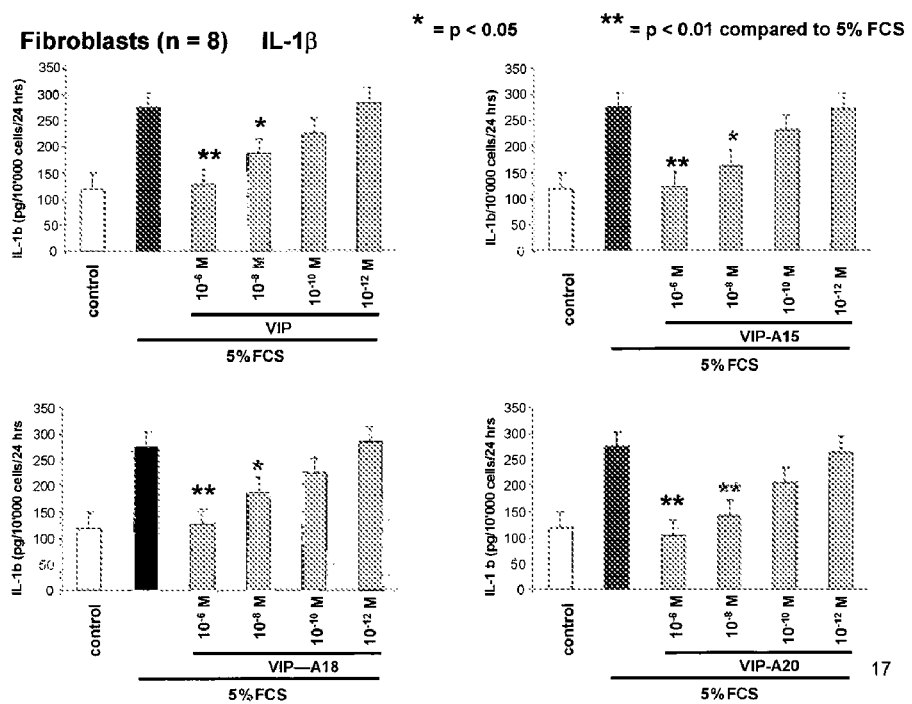
FIG. 12b depicts the effect of SEQ ID No.:1 (VIP) as compared to SEQ ID No.:2 (A-15), SEQ ID No.:3 (A-18) and SEQ ID No.:4 (A-20) on the Interleukin (IL)-1β production in fibroblasts in vitro.
Figure 13:
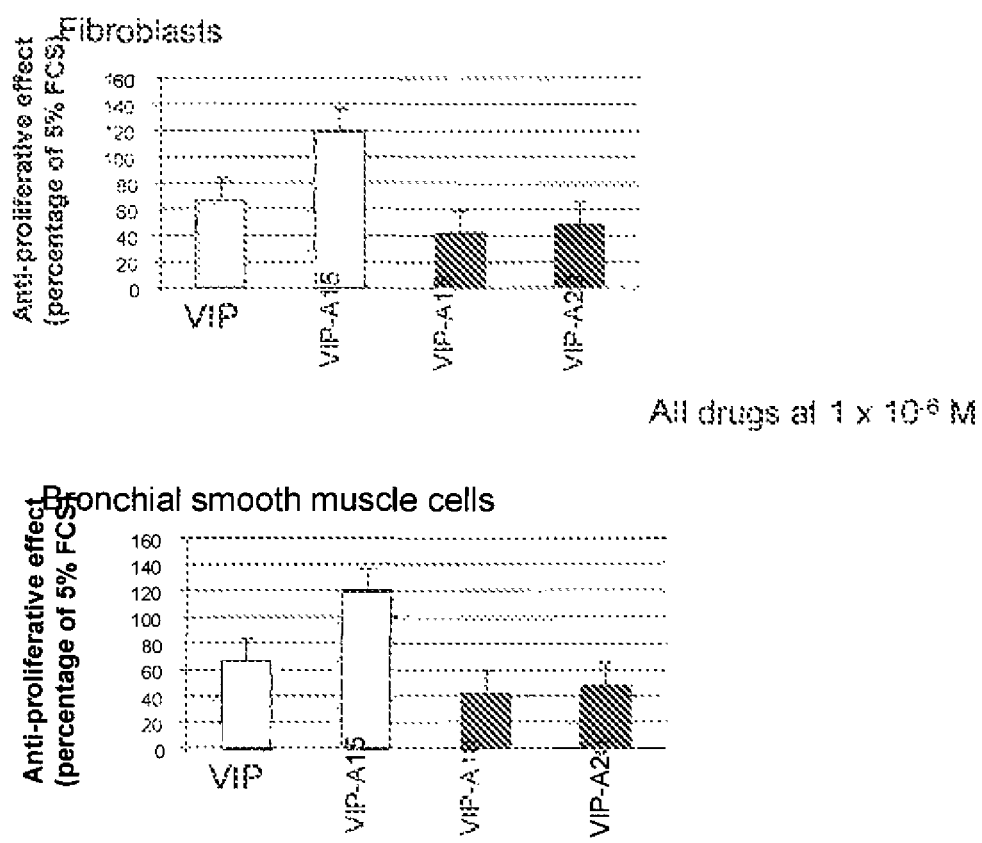
FIG. 13 depicts the anti-proliferative effect of SEQ ID No.:1 (VIP) as compared to SEQ ID No.:2 (A-15), SEQ ID No.:3 (A-18) and SEQ ID No.:4 (A-20) on fibroblasts and bronchial smooth muscle cells.

In COPD, VIP serum concentrations were lower compared to controls (FIG. 1). Thirty (88%) patients completed the study (Table 1). Post-bronchodilator forced expiratory volume in 1 second (FEV1) significantly improved with VIP by 0.107 L and vital capacity (IVC) by 0.160 L compared with placebo (p<0.01) (FIG. 2). According to the short 36-item questionnaire (SF-36) developed for medical outcomes studies, the improvement in quality of life was greater with VIP (4.08) than with placebo (0.20) (Table 2). Similarly, Borg dyspnea scale result was greater with VIP (−0.20 units at rest and −1.07 after exercise) than with placebo (0.21 units at rest and 0.43 units after exercise) (FIG. 3); exercise capacity increased by 32.7 m (p<0.01) in the VIP group as compared to placebo group (−8.6 m) using the six minutes walking test (FIG. 4). Ten exacerbations with placebo and only 8 with VIP were observed (Table 3).

VIP is a safe and effective drug for treatment of COPD, it reduces exacerbations, improves lung function, and health-related quality of life. Long-term studies are needed, however, to fully assess its efficacy in COPD.

Example 2

VIP and Cystic Fibrosis

The airway inflammatory response in CF is persistently neutrophilic, marked by upregulation of neutrophil chemotactic mediators such as interleukin 8 (IL-8) and leukotriene B4 (LTB4); florid accumulation of neutrophils in the airways; and neutrophil activation, with release of toxic products such as neutrophil elastase. The initial inflammatory response to most bacterial stimuli, in the lung and elsewhere, is "acute", that is, neutrophil dominant such as the inflammation by COPD. Two CF patients were treated with 200 μg VIP daily, per inhalation and measured their lung function for and after 3 months treatment by VIP. Post-bronchodilator forced expiratory volume in 1 second (FEV1) and vital capacity (VC) significantly improved with VIP treatment after 3 months (Table 4).

Example 3

Therapeutic Potential of VIP and the Peptides According to the Invention

The combination of low serum VIP levels in COPD patients, the VIP receptor up-regulation in chronic bronchitis patients, the pleiotrope anti-inflammatory effects of VIP, the possibility for local administration and the lack of local and systemic side effects in our trial, makes VIP a promising candidate for treatment of COPD and CF. Furthermore the inventors synthesized the synthetic peptides according to the invention, preferably peptide SEQ ID No.:2 (A-15), SEQ ID No.:3 (A-18) and SEQ ID No.:4 (A-20) with new structure and compared their anti-inflammatory and vasodilatory properties with VIP in vitro by the methods described in the following examples. The synthesis of the peptides according to the invention was carried out by known standard methods.

Example 4

In Vitro Macrophage Generation

Peripheral blood mononuclear cells were isolated from whole venous blood from 12 stable COPD patients and 12 healthy probands by Ficoll density gradient centrifugation. Monocytes were differentiated in RPMI-1640 medium supplemented with 5% FCS, antibiotics and $10^{-8}$ M 1,25-dihydroxycholecalciferol (Sigma) in a humidified atmosphere with 5% $CO_2$ at 37° C.

Example 5

In Vitro LPS Incubation

For infection simulation, macrophage stimulation and experimental in vivo treatment the differentiated cells were incubated either with LPS, with LPS and SEQ ID No.:1 (VIP) or SEQ ID No.:2 (A-15) or SEQ ID No.:3 (A-18), or with medium alone for control.

Example 6

Nitric Oxide (NO) Secretion Determination

To test the hypothesis whether or not the macrophages utilize the VIP-signaling pathway to modulate and limit the immune response, the inflammation reaction in vitro was stimulated and NO (produced by iNOS) production by the cells was measured under inflammation and under in vitro therapy with VIP and the peptides according to the invention (SEQ ID Nos 2 and 3). NOS increased dramatically by LPS after 24 hours. Simultaneous incubation of LPS with VIP and the peptides according to the invention revealed a marked anti-inflammatory response found after 24 hours (Table 5). This anti-inflammatory response was better by both VIP-analogues according to SEQ ID Nos. 2 and 3.

Example 7 cAMP Measurement

Effects of VIP and the peptides according to the invention are mediated by specific G-protein coupled receptors. Three distinct receptor subtypes, with differing affinity for the peptides, have been cloned and characterized as receptors 1 and 2 (VPAC1 and VPAC2) and pituitary adenylate cyclase activating polypeptide receptor (PAC1). The secondary messenger is cyclic adenosine mono phosphate (CAMP).

The capacity of VIP and the peptides according to the invention (SEQ ID No 2 and 3) on cAMP regulation were compared by following methods:

Cells derived from pulmonary artery (PASMC) were seeded in 24 well plates and cultured in DMEM containing 10% fetal calf serum (Gibco lifesciences, Karlsruhe), Penicillin (Gibco lifesciences, Karlsruhe, 100 U/ml) Streptomycin (Gibco lifesciences, Karlsruhe, 100 U/ml) to confluency. After serum starvation for 3 hours cells were incubated with VIP or the peptides according to the invention with or without 3-isobutyl 1-methyl xanthine for 20 min which has been shown to be the optimal incubation time for analysis of cyclic AMP production.

VIP increases the cyclic AMP content of PASMC. Higher increase were observed after stimulation with the novel peptides according to the invention (SEQ ID No. 2 and 3) (Table 6a, 6b and 6c).

Example 8

Elisa Assays and IL-4, IL-6, IL-8, IL-10, IL1-b und TNF-a Measurement in Fibroblasts and Bronchial Smooth Muscle Cells after FCS Stimulation In Vitro Elisa assays for IL-4, IL-6, IL-8, IL-10, IL1-b und TNF-a were performed according to the manufactures instructions (BD-PharMingen). The cytokine secretion under FCS stimulation in each experiment was set to 100% for each cell donor and experiment. All other results were expressed relative to 100%. For statistical analysis we used paired Student's t-test, or the Wilcoxon signed rank test.

TABLE 1

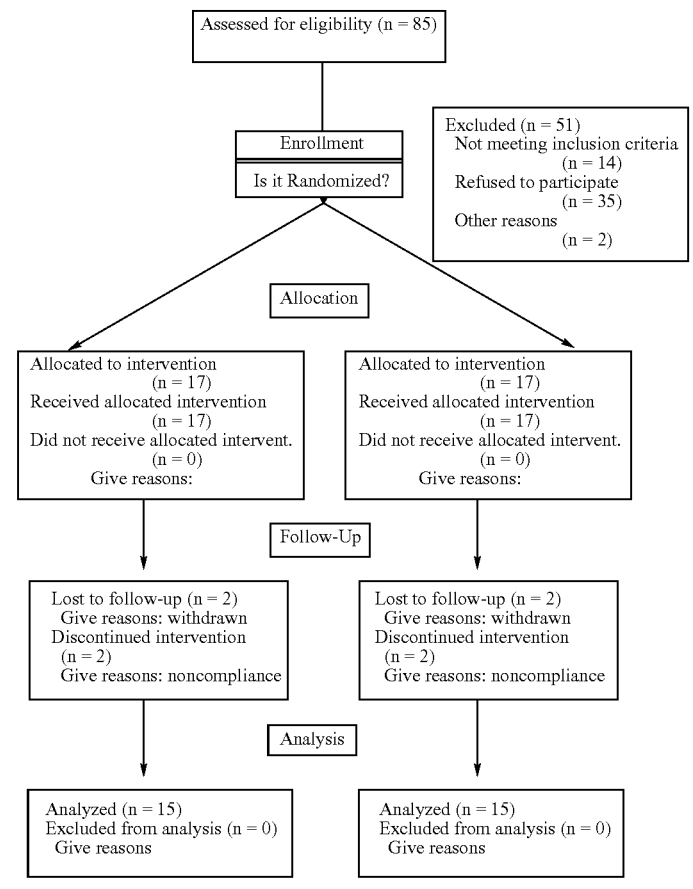

The Consort E-Flowchart of the clinical study

The incubation is stopped by rinsing cells with PBS and immediate lysis of cells with HCl (0.1N) containing 3-isobutyl 1-methyl xanthine (500 µM) to block further hydrolysis of cAMP.

Lysed cells were centrifuged and the supernatants assayed for cAMP using an commercially available cyclic AMP ELISA (Assay Designs, Inc., Michigan, distribution by Bio Trend, Köln).

TABLE 2

Quality of life according to the short 36-item questionnaire - SF-36.

| SF-36 | VIP | Placebo |
| --- | --- | --- |
| PHS at baseline | 41.15 ± 2.26 | 38.62 ± 2.12 |
| PHS after treatment | 45.23 ± 2.07 | 38.82 ± 2.49 |

TABLE 2-continued

Quality of life according to the short 36-item questionnaire - SF-36.

| SF-36 | VIP | Placebo |
|---|---|---|
| MHS at baseline | 44.45 ± 2.41 | 44.89 ± 2.53 |
| MHS after treatment | 47.92 ± 2.18 | 45.64 ± 3.18 |

TABLE 3

Adverse events

| | Placebo (n = 15) | | VIP (n = 15) | |
|---|---|---|---|---|
| COPD exacerbation | 10 | (66.7%) | 8 | (53.3%) |
| Nasopharyngitis | 1 | (6.7%) | 0 | (0%) |
| Diarrhoea NOS | 1 | (6.7%) | 0 | (0%) |
| Upper respiratory tract infection | 1 | (6.7%) | 1 | (6.7%) |
| Nausea | 0 | (0%) | 0 | (0%) |

TABLE 4

Lung function of CF patient for and after VIP treatment
Patient: D. G., 19 J., F., CF

| | TLC | VC | FEV1 | FEV1/VC | RV | PaO2 | PaCO2 |
|---|---|---|---|---|---|---|---|
| Measuring1 | 5.54 | 2.21 | 0.95 | 43 | | | |
| Measuring2 | 5.40 | 2.27 | 1.10 | 48 | | | |

TABLE 5

Nitrit production by monocytes after LPS stimulation by VIP and VIP analogs

| | 1 | 2 | 3 | 4 | 5 |
|---|---|---|---|---|---|
| LPS 100 [nM] | − | + | + | + | + |
| VIP 100 [nM] | − | − | + | − | − |
| Pep - 15 100 [nM] | − | − | − | + | − |
| Pep - 18 100 [nM] | − | − | − | − | + |
| Nitrit [μmol] +/− SD | 48 +/− 7 | 75 +/− 18 | 31 +/− 9 | 16 +/− 8 | 19 +/− 7 |

TABLE 6a cAMP in PASMC after VIP stimulation for 20 min.

| | 1 | 2 | 3 | 4 | 5 | 6 | 7 | 8 | 9 |
|---|---|---|---|---|---|---|---|---|---|
| VIP [nM] | − | − | 1 | 10 | 100 | 1 | 10 | 100 | − |
| IBMX 500 μM | − | + | − | − | − | + | + | + | + |
| Forskolin 10 μM | − | − | − | − | − | − | − | − | + |
| cAMP [pmol/ml] +/− SD | 2.70 +/− 2.40 | 16.37 +/− 7.21 | 11.18 +/− 9.17 | 13.80 +/− 8.08 | 19.50 +/− 7.14 | 20.11 +/− 10.01 | 23.52 +/− 12.15 | 27.78 +/− 10.45 | 41.10 +/− 14.31 |

TABLE 6b cAMP in PASMC after Pep 15 stimulation for 20 min.

| | 1 | 2 | 3 | 4 | 5 | 6 | 7 | 8 | 9 |
|---|---|---|---|---|---|---|---|---|---|
| Pep - 15 [nM] | − | − | 1 | 10 | 100 | 1 | 10 | 100 | − |
| IBMX 500 μM | − | + | − | − | − | + | + | + | + |
| Forskolin 10 μM | − | − | − | − | − | − | − | − | + |
| cAMP [pmol/ml] +/− SD | 3.4 +/− 1.25 | 17.16 +/− 6.92 | 13.30 +/− 7.18 | 16.30 +/− 10.10 | 23.30 +/− 11.14 | 26.45 +/− 11.06 | 27.00 +/− 12.10 | 36.67 +/− 12.18 | 47.81 +/− 14.81 |

TABLE 6c cAMP in PASMC after Pep 18 stimulation for 20 min.

| | 1 | 2 | 3 | 4 | 5 | 6 | 7 | 8 | 9 |
|---|---|---|---|---|---|---|---|---|---|
| Pep - 18 [nM] | − | − | 1 | 10 | 100 | 1 | 10 | 100 | − |
| IBMX 500 μM | − | + | − | − | − | + | + | + | + |
| Forskolin 10 μM | − | − | − | − | − | − | − | − | + |
| cAMP [pmol/ml] +/− SD | 2.2 +/− 2.4 | 15.91 +/− 5.72 | 14.83 +/− 7.52 | 19.45 +/− 10.11 | 28.43 +/− 7.19 | 36.66 +/− 13.42 | 37.00 +/− 12.11 | 46.42 +/− 10.0 | 58.00 +/− 14.13 |

The invention claimed is:

1. A method of treating lung diseases comprising administering to a patient suffering from said diseases a synthetic peptide in a pharmacologically effective amount selected from the group consisting of

```
                                              (SEQ ID NO: 2)
(i) His(Ac)-Ser-Asp-Ala-Val-Phe-Thr-Asp-Asn-Tyr-

Thr-Arg-Leu-Arg-Lys-Gln-Met(O)-Ala-Val-Lys-Lys-Tyr-

Leu-Asn-Ser-Ile-Leu-Asn, (SEQ ID NO: 3)
(ii) His(Ac)-Ser-Asp-Ala-Val-Phe-Thr-Asp-Asn-Tyr-

Thr-Arg-Leu-Arg-Lys-Gln-Met-Ala-Val-Lys-Lys-Tyr-

Leu-Asn-Ser-Val-Leu-Asn,
and (SEQ ID NO: 4)
(iii) His(Ac)-Ser-Asp-Ala-Val-Phe-Thr-Asp-Asn-Tyr- Thr-Arg-Leu-Arg-Lys-Gln-Met(O)-Ala-Val-Lys-Lys-Tyr- Leu-Asn-Ser-Val-Leu-Asn,
``` wherein His(Ac) means N-acetyl histidine, and Met(O) means methionine oxide, and wherein the synthetic peptide has the biological activity of vasoactive intestinal peptide (VIP), and its administration to said patient leads to an improvement of lung functions in the patient compared to the administration with VIP under comparable conditions.

2. The method of claim 1, wherein the administration of the synthetic peptide or said pharmaceutical composition leads to an increased serum half-life in the patient as compared to VIP.

3. The method of claim 1, wherein said peptide is provided into the lung of the patient by inhalation of the peptide formulated as an aerosol.

4. The method of claim 1, wherein the disease is selected from the group consisting of COPD, cystic fibrosis (CF), and bronchiolitis obliterans (BO).

5. The method of claim 4, wherein the disease is COPD that is functionally uncoupled from or pharmacologically not correlated to hypertension diseases.

6. The method of claim 1, wherein the peptide is the peptide of SEQ ID NO: 2.

7. The method of claim 1, wherein the peptide is the peptide of SEQ ID NO: 3.

8. The method of claim 1, wherein the peptide is the peptide of SEQ ID NO: 4.

9. The method of claim 1, wherein the improvement is between 20-30%.

* * * * *